United States Patent [19]
Klein et al.

[11] Patent Number: 5,529,490
[45] Date of Patent: Jun. 25, 1996

[54] MEDICAL TOOL DISPENSER SYSTEM

[76] Inventors: Douglas J. Klein, 17681 Crestline Dr.; Paul E. Klein, 928 Lake Shore Rd., both of Lake Oswego, Oreg. 97034

[21] Appl. No.: 414,774

[22] Filed: Mar. 31, 1995

Related U.S. Application Data

[63] Continuation of Ser. No. 154,967, Nov. 19, 1993, abandoned, which is a continuation-in-part of Ser. No. 7,374, Jan. 20, 1993, Pat. No. 5,326,260, which is a continuation-in-part of Ser. No. 716,308, Jun. 17, 1991, abandoned.

[51] Int. Cl.⁶ .................................................. A61C 3/00
[52] U.S. Cl. .............................. 433/3; 433/11; 206/63.5; 206/805; 221/307
[58] Field of Search ................................ 221/20, 25, 70, 221/305, 307, 309, 310; 433/3, 4, 11, 13, 18; 225/51, 52, 13; 132/321, 323; 206/338, 339, 343, 369, 370, 409, 805

[56] References Cited

U.S. PATENT DOCUMENTS

| | | | |
|---|---|---|---|
| 2,989,212 | 6/1961 | Ekenstam et al. | 221/25 |
| 3,791,601 | 2/1974 | Broden | 206/409 |
| 3,903,601 | 9/1975 | Anderson et al. | 206/820 |
| 4,004,683 | 1/1977 | Pomeroy et al. | 206/3 |
| 4,034,770 | 7/1977 | Trecker . | |
| 4,038,753 | 8/1977 | Klein . | |
| 4,106,374 | 8/1978 | Dragan | 221/36 |
| 4,172,523 | 10/1979 | Weglage | 221/307 |
| 4,277,236 | 7/1981 | Kurz | 433/3 |
| 4,330,271 | 5/1982 | Anderson | 433/3 |
| 4,385,890 | 5/1983 | Klein | 433/4 |
| 4,436,510 | 3/1984 | Klein | 433/4 |
| 4,881,560 | 11/1989 | Blank et al. | 132/324 |
| 4,946,385 | 8/1990 | Eckert et al. | 433/2 |
| 4,946,386 | 8/1990 | Kidd et al. | 433/18 |
| 5,013,238 | 5/1991 | Sterret et al. | 433/2 |
| 5,016,766 | 5/1991 | Klein | 221/22 |
| 5,326,260 | 7/1994 | Klein et al. | 433/11 |
| B14,217,686 | 6/1986 | Dragan | 29/413 |

OTHER PUBLICATIONS

3M Unitek Alastik MiKro–StiK Dispensing System for Ligatures and Chains, 1994.

*Primary Examiner*—Cary E. O'Connor
*Attorney, Agent, or Firm*—Kolisch, Hartwell, Dickinson, McCormack & Heuser

[57] ABSTRACT

A presenting/dispensing system for chain-interconnected, cut-separable orthodontic/medical devices, organized into groups having a pre-selected number of patient-usable units, including a container constructed for housing such devices, and presenting/dispensing aperture substructure formed therein to allow for presenting such devices and dispensing a desired number of the same in an indexed manner. The system also includes check structure associated with the presenting/dispensing aperture substructure, which check structure is changeable, as a result of dispensing action, to a first condition that accommodates dispensing of such devices, and to a second condition, upon termination of such action, that resists slipping back of a chain of devices into the container.

7 Claims, 2 Drawing Sheets

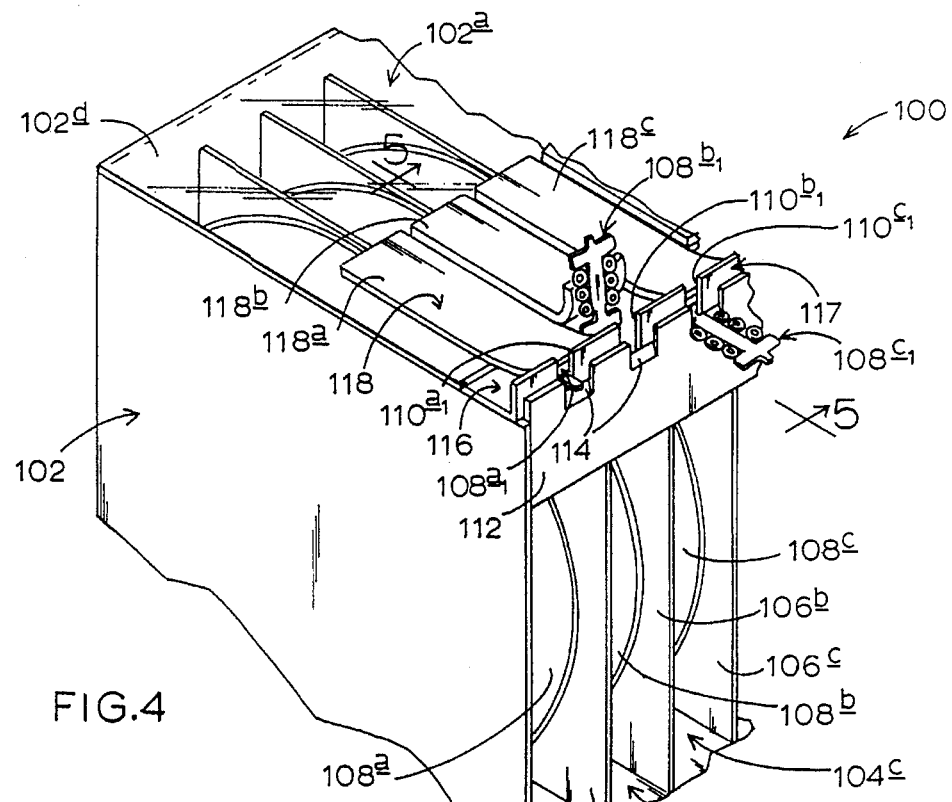
FIG.4
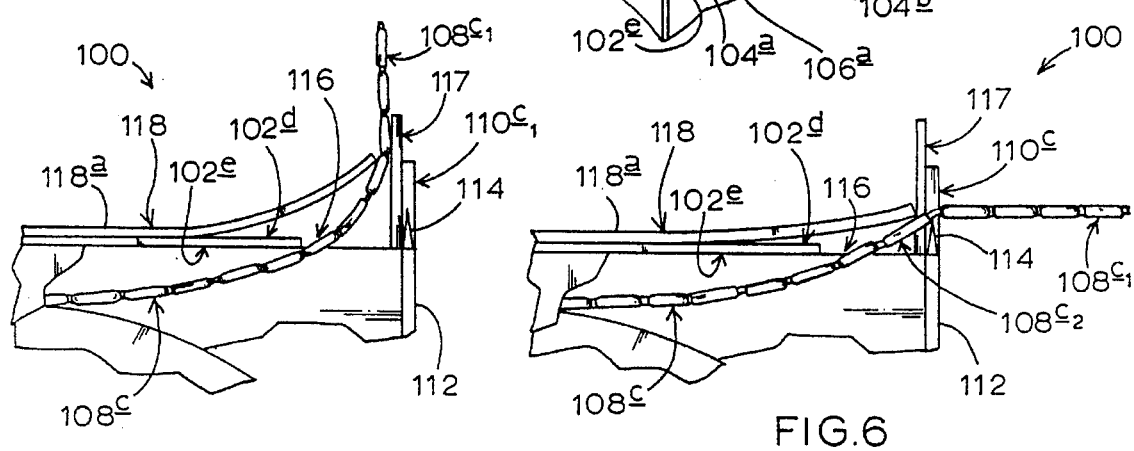
FIG. 5
FIG.6
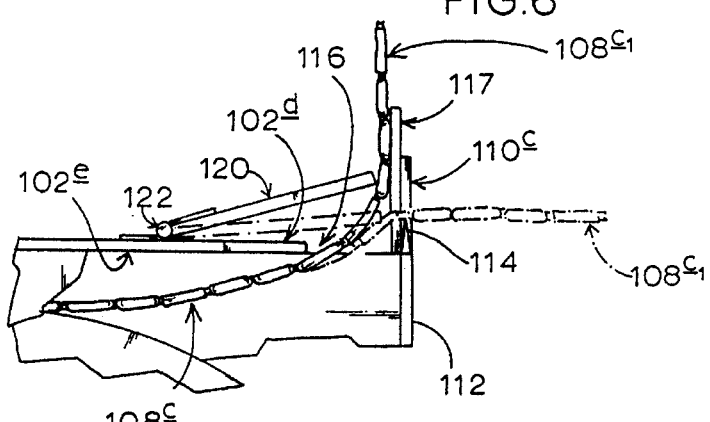
FIG.7

MEDICAL TOOL DISPENSER SYSTEM

CROSS-REFERENCE TO RELATED APPLICATIONS

This is a continuation of application Ser. No. 08/154,967, filed Nov. 19, 1993, abandoned, which is a continuation-in-part of application Ser. No. 08/007,374, filed Jan. 20, 1993, now U.S. Pat. No. 5,326,260, which, in turn, is a continuation-in-part of application Ser. No. 07/716,308, filed Jun. 17, 1991, abandoned.

BACKGROUND AND SUMMARY OF THE INVENTION

The present invention relates to a presenting/dispensing system for interconnected, cut-separable orthodontic/medical devices which may incorporate the same in the form of a spooled or serpentine-folded chain containing plural seriatim-joined devices. More particularly, it relates to such a system which is designed specifically for handling to-be-dispensed devices which carry, as indexed groupings of selected numbers of units, intra-oral orthodontic elastomeric tools, such as ligators, separators and others—a setting in which the invention has been found to offer particular utility. Accordingly, a preferred embodiment of the invention is described in conjunction with dispensing such things.

Effective elastomeric orthodontic tools of the type generally mentioned above have been available for years, and various techniques, apparatuses and arrangements have been proposed for enabling dispensing of the same. For example, prior art patents dealing with the latter include U.S. Pat. Nos. 3,903,601 to Anderson et al., 4,038,753 to Klein, 4,330,271 to Anderson, and 5,016,766 to Klein et al.

In the dispensing and handling schemes proposed in the past, there are several common characteristics which, while useful and appropriate in many instances, are not so useful and appropriate in others. For example, ligators, such as O-ring ligators, or separators have been presented in the past (1) as completely free units which are plucked from a container holding the same, (2) as free (non-co-joined) individuals contained on a dispensing wand or the like, (3) in elongate chains of individual, separable units, and (4) in relatively large arrays of units joined integrally with an elongate dispensing element. Examples of the latter are found in the '753 and '271 patents mentioned above.

Generally speaking, practitioners have found useful a handling and dispensing arrangement in which an elongate dispensing body carries integrally joined, but cut-away- or break-away-separable, orthodontic tools.

Considering how this kind of structure has been manufactured in the past, and can be manufactured, in order to obtain dispensable tools which are easily handled and best suited for their intended purposes, manufacturing procedures have generally divided into two generic categories including molding, and stamping (or cutting) from previously formed sheet elastomeric material. Among the advantages of devices produced by a stamping procedure is that long chains of devices can be produced, and these chains are easily and very desirably held for dispensing in a spooled condition, a serpentine stacked condition, and the like. However, stamped units do not offer the opportunity to create orthodontic tools that vary in cross-sectional dimension and that have smoothly rounded outside surfaces at all desired locations. Further, stamp cutting according to prior art procedures does not, in all instances, offer the most desirable degree of control over final unit dimensions.

Molding, inter alia, offers the opportunity to overcome the disadvantages just mentioned in stamping, but does not easily lead to the molded creation of long easily-dispensable chains of devices.

A hybrid approach to the manufacturing of devices of the type discussed specifically herein blends the advantages of molding with the "chaining" advantage of stamping, via the process of pre-molding pre-selected unit lengths of devices, and then suitably joining these, in an end-to-end (endo) fashion, to create spoolable (serpentine stackable, etc.) chains of any desired length.

Those familiar with the practice of orthodontics will recognize that, for different specific procedures, one typically requires for use a specific group number of devices—usually no more and no less. For example, unit groupings containing two, four or six units of specific character are typical. It is with this in mind that we think of our system as one which is designed in a manner that uniquely enables the handling and dispensing of devices which are presented in a spool as indexed groupings of selected numbers of units, separable as a grouping which contains essentially precisely the exact number of tools or devices which the practitioner needs for a particular procedure. As will become apparent, and while we have mentioned different common grouping numbers, we illustrate herein a system dispensing, from a chain, indexed groupings containing six working units, or tools.

Interweaving today with the issue of convenient handling and dispensing is the issue of preventing patient cross-contamination resulting from at-risk exposure of intra-oral tools prior to placement for intra-oral use.

Dispensing and handling systems/devices of the type in the past characterized by a long dispensing finger, or rod, containing multiple detachable tools, such as ligators, often include a far greater number of tools than an orthodontist actually requires during a particular patient-specific treatment procedure (note the indexed-grouping-advantage discussion above). Accordingly, where, even in a carefully controlled hygienic setting that enables patient-specific dispensing of one or two only of such tools in an exposed environment, there is substantial waste which results when only a few tools are removed for use, and the remainder are tossed out in keeping with cross-contamination hygiene practice.

Giving an illustration relating to the use of ligators, for example, experiences indicate (as mentioned earlier) that there are many procedures (like less-than-full-arch procedures) in which only a very few ligators are required, a setting wherein it is desirable to be able to place, in an at-risk (for contamination) environment, a dispensing/handling device, which carries only a small number of available ligators, thus to minimize wasteful discarding of exposed but unused ligators. Multiple devices each containing small numbers of ligators can always be brought into play where greater numbers of ligators are required for a given procedure, still without leading to excessive waste.

Cross-referenced application Ser. No. 08/007,374 provides just such a unique hand-holdable, tool-dispensing device for medical tools, such as orthodontic O-ring ligators or other devices, which takes this latter consideration into account in a very practical, simple, economical and satisfactory manner.

With respect to storing and dispensing such devices, there is a need for a system that can be used to accomplish such functions without bringing into a contamination environment an unwanted number of such devices.

A general object of the present invention is to provide a unique system for dispensing such devices in a manner that safeguards against bringing into a contamination setting a greater amount of such devices than is needed for the particular job at hand.

A further object is to provide such a system that presents and dispenses such devices, from a long chain of the same, in a manner (indexed groupings of selected numbers of units) that minimizes wasteful discarding of exposed but unused ligators.

According to the system of the present invention, such an elongate chain of devices may be stored conveniently either as a spool, or as a folded serpentine "stack", within the interior of a contamination-barrier container for enabling device-by-device (group-by-group) withdrawal through presenting/dispensing aperture substructure formed therein to allow for presenting such devices and dispensing a desired grouped number of the same. The chain which we illustrate herein may be made either in accordance with the conventional stamp-cutting procedure mentioned earlier, or by the "hybrid" procedure involving molding and endo joining of shorter lengths of groupings of devices.

The system of the present invention also includes check structure associated with the presenting/dispensing aperture substructure, which check structure includes a swingable paddle, or flap, that acts with what can be thought of as "toggle-like" pinching action against an expanse of the broad face of an anvil to lock the exposed end of a chain against slipping unwantedly back into the dispensing container.

These and other objects and advantages that are attained by the invention will become more fully apparent as the description which now follows is read in conjunction with the accompanying drawings.

DETAILED DESCRIPTION OF THE DRAWINGS

FIG. 4 is a fragmentary isometric view illustrating the presenting/dispensing system of the present invention including to-be-dispensed devices stored in the form of an elongate spool accessible from a dispensing container via presenting/dispensing aperture substructure, and with a desired device being cut-separable from the chain via a cutter blade positioned on the container outward of the slot.

FIG. 5 is an enlarged, fragmentary, upper-side sectional view taken generally along line 5—5 in FIG. 4, focusing attention on a preferred embodiment of the presenting/dispensing system of the invention.

FIG. 6, which is like FIG. 5, focuses attention both on a cutting operation that can be performed using the invention, and on the toggle-like pinch-locking action performed in the nip region between a flap and an expanse of a broad, generally planar face in an anvil in the system.

FIG. 7, which is like FIGS. 5 and 6, shows another embodiment of the invention.

DETAILED DESCRIPTION OF, AND BEST MODE FOR IMPLEMENTING, THE INVENTION

Figure 1:
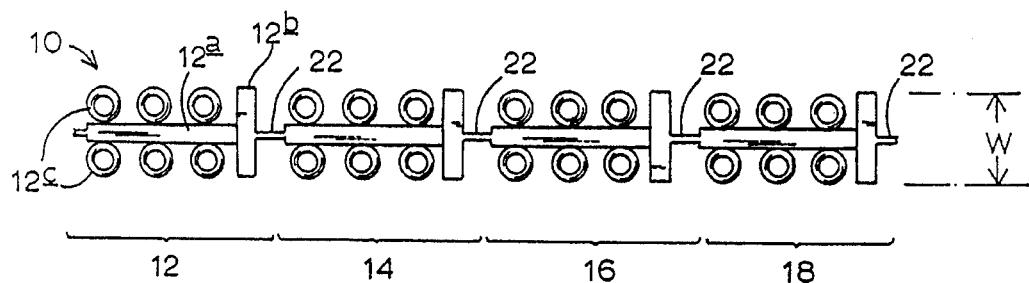
FIG. 1 is a fragmentary plan view of a length of an elongate elastomeric chain containing individually separable, indexed orthodontic medical devices constructed in accordance with the teachings of cross-referenced application Ser. No. 08/007,374.
Figure 2:
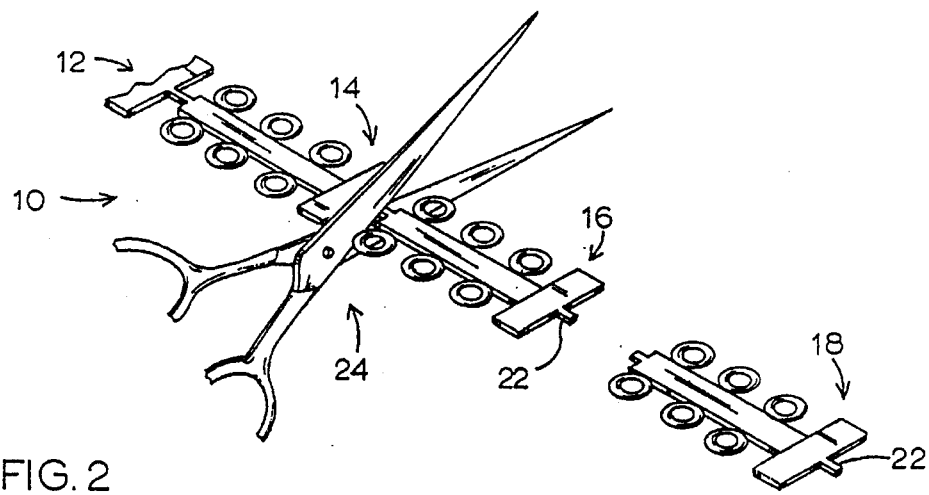
FIG. 2 is an isometric view of the chain fragment of FIG. 1, illustrating pre-separation and post-separation of individual unit groups from the chain via manual scissors-effected separation.
Figure 3:
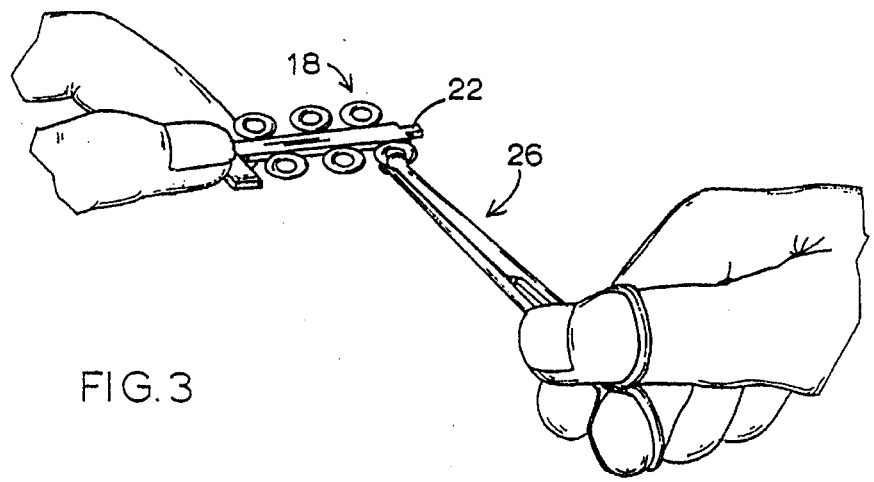
FIG. 3 is a fragmentary isometric view illustrating handling and manipulation of an individual group device during a procedure with a patient.

Turning now to the drawings, FIGS. 1–3, inclusive, show the type of interconnected, cut-separable orthodontic/medical, grouped-tool devices that are preferably used in and with the system of the present invention. These devices are organized in an elongate chain which may be either of the stamped-cut variety, or of the above-described hybrid variety. Since, in most instances, molding is a preferred manner of making the ultimately used intra-oral units, we illustrate and describe the invention hereinbelow in that setting.

Referring first of all to FIG. 1, indicated generally at 10 is a fragment of an elongate, homogeneous, unitary, elastomeric chain, which is a molded chain, formed from endo-joined molded pieces. Chain 10 includes plural, tool-dispensing medical devices, each being individually separable, as will be explained, and each carrying, in a group having a pre-selected number of units (six herein), plural tools (ligators) for use during an orthodontic ligating procedure. Specifically shown in FIG. 1, in the fragment illustrated, are four such devices, designated 12, 14, 16, 18. Referring for illustration purposes to device 12, each device is characterized by having a carrier body with an elongate, slender, finger-like portion, such as portion 12a, one end of which is joined integrally to elongate, broad-expanse, bar-like, handle/positioner structure 12b. Structure 12b is also preferably generally flat and planar to promote ease of storing, dispensing and handling. Carrier body 12 has what may be thought of as a T-shaped configuration formed by the joinder of portion 12a with structure 12b. Joined integrally to the opposite sides (top and bottom as shown) of body 12a are six orthodontic O-ring ligators, or tools, such as tools 12c.

The devices in chain 10, other than those devices which, at a given point in time, make up the opposite ends of the chain, are joined seriatim to two other devices through reduced-dimension, or weakened, regions, such as those shown at 22 in FIG. 1. The presence of such weakened regions is preferable to facilitate device separation, but not absolutely necessary. The central region 22 shown in FIG. 1 is a region of endo joinder between two molded pieces.

The overall width of each device in chain 10, as the same is viewed in FIG. 1, is indicated at W. The reason for mentioning this will become apparent shortly.

As was stated earlier, there are various orthodontic ligating procedures in which it is not necessary that an orthodontist have readably available, and in an exposed environment, enough individual ligators to handle a full arch or more of a patient's mouth. Nevertheless, various prior-art systems which present ligators for dispensing from carrier systems often make available at least a full arch complement (in number) available all at once. Where only a minor number of ligators is actually required for use, and to assure proper guard against patient cross-contamination, carriers bearing a large number of unused ligators are often simply thrown away and thus wasted after such a limited procedure.

Recognized in the underlying implementation of the structure of the present invention is that presentation of dispensable ligators (or other tools) in small groups makes possible proper attention to patient cross-contamination avoidance, as well as to ligator-waste avoidance. While the exact "small" number of made-available ligators is a matter of choice, we have found that a very suitable small-number, made-available amount falls typically within the range of two to six ligators.

Preferably, plural, seriatim-joined devices, containing the small number of ligators just mentioned, are fabricated in the chain fashion indicated in FIG. 1 for manufacturing simplicity and economy, and ultimately for ease of dispensing and handling. Preferably also, a prepared chain of separable devices is designed to be handled in such a fashion that selected devices can be exposed to a contaminating environment only on what can be thought of as an indexed, device-by-device basis for separation of individual devices for ultimate use.

FIG. 2 illustrates just very generally how separation may occur, in which figure, device 18 is shown cut-separated from device 16, and device 16 is shown about to be cut-separated from device 14 by scissors shown at 24. These separation steps will typify a procedure wherein an orthodontist has concluded that he or she will require up to twelve ligators (six per device). Accordingly, two and only two devices are separated from the chain and exposed in the environment where contamination could occur. FIG. 2, which is simply generically illustrative of a separation operation, does not specifically illustrate a contamination barrier to isolate still-to-be-used devices 12, 14, and others (undepicted) in chain 10. A proper contamination barrier for presenting and allowing dispensing will be discussed shortly.

FIG. 3 illustrates how, typically, a separated device, and here device 18 is depicted, is used in the hands of an orthodontist during a ligating procedure. In FIG. 3, the left hand is shown gripping the handle portion of the device, and the right hand is shown employing a hemostat 26 to separate one of the group of six ligators (tools) carried on the carrier body in device 18. Pull-away, or snap-away, separation of each ligator is facilitated by the presence in the units of the invention of relatively small connecting isthmuses (not shown) extending between each ligator and the associated central finger portion of the carrier body. Obviously, the handle portion makes for convenient handling, with the orthodontist not being required directly to touch an about-to-be-removed ligator.

Referring to FIGS. 4–6, attention is now focused on the presenting/dispensing system of the present invention which is indicated generally at 100. System 100 includes a container 102 constructed for housing devices like those described above. As will be explained, container 102 cooperates with chains, each being like chain 10, to afford a system that attends to the matter of patient cross-contamination. Container 102 is preferably a suitably stand-anchored, plastic dispensing container with partitions dividing the container into dispenser sections, each for holding individual spools of chain, like previously discussed chain 10. Three such dispenser sections are shown at 104a, 104b, 104c, and three partitions are shown at 106a, 106b, 106c. A somewhat analogous array of presentation/dispensing containers (for another type of orthodontic apparatus) is illustrated and described in above-mentioned U.S. Pat. No. 5,106,766, and reference is herein made to that patent for the reader's aid in understanding, generally, a similar kind of anti-contamination system. There is no special requirement that spooled chains be used, and those skilled in the art will appreciate that serpentine stacking, and other folding techniques, are also possible to store chains of medical devices for dispensing in accordance with the present description.

Focusing attention on dispenser section 104a, the same herein includes a suitable, somewhat upright, rectilinear space, within which is stored a chain 108a, like chain 10, with the former wound on a spool residing within the section. It is a matter of choice whether such a spool is supported or not on a hub. While not depicted in FIG. 4, this chain, progressing from the center of the spool, wraps in a clockwise direction from the center toward the outside of the spool, with the end of the chain containing devices next-to-be-dispensed residing near the top of the spool, and extending into what might be thought of as a pre-dispense condition adjacent a blocking/interference slot, such as slot $110a_1$ formed in the top of the front of section 104a. Slot $110a_1$ has a width which is less than previously mentioned width W. Referring for a moment to FIG. 5, just such a predispense condition of chain 108c is depicted adjacent slot $110c_1$.

Formed near the top of section 104a (and to-be-described sections 104b–c) is resident cutting structure including a sheath-like unit 112 which supports plural cutter blades 114, one blade for each dispenser section. This structure is used, as will be explained, to separate device groups from respective chains, such as chains 108a, 108b, 108c. Such cutting structure facilitates single-hand access to, and cut-separation of, selected devices.

Continuing with the description of container 102 in FIGS. 4–6, a suitably attached top 102a is formed with an access opening 116. That opening and slots $110a_1$, $110b_1$, $110c_1$ may be thought of together as presenting/dispensing aperture substructure formed in container 102 to allow for presenting devices and dispensing a desired number of them. Top 102a may be transparent as depicted, as may be the entirety of container 102. Opening 116 is defined, collectively, by an anvil-like substructure (or anvil) 117 and by top 102a. Anvil-like substructure 117 is formed with previously mentioned slots $110a_1$, $110b_1$, $110c_1$.

Still referring to FIGS. 4–6, container 102 also includes a check structure 118 which is associated with the presenting/dispensing aperture substructure. In the embodiment of the invention now being described, check structure 1118 takes the form of a flap 118a made of a suitable flexible material, which flap is joined as by bonding to the upper surface of top 102a, and which has a free end (the right end as pictured in FIGS. 5 and 6) which overlies opening 116 and confronts anvil 117. As will become apparent from the description that now ensues, the free end of flap 118a defines what is referred to herein as a nip region with an expanse in the confronting broad face of anvil 117, freely allowing withdrawing of chain $108c_1$ to dispense devices, and thereafter acting with what can be thought of as toggle-like action to pinch-lock the chain in the nip region between it and the anvil, thus to lock the chain against unwanted slipping back into the dispensing container.

FIG. 5 in the drawings illustrates the free end of flap 118a during dispensing action in what is referred to herein as a first condition that accommodates free drawing out and dispensing of devices. FIG. 6 illustrates the free end of the flap in what is referred to herein as a second condition wherein, effectively, it pinches chain 108c against anvil 117 and prevents the chain from slipping by gravity back into the interior of container 102.

Shifting attention for a moment to FIG. 7, and as an alternative, check structure 118 may be constructed as paddle-like structure 120 which is formed with a material that is suitably rigid, and which is connected to the top of container 102 via a hinge 122. Paddle 120 is changeable between a first condition (shown by solid lines in FIG. 7) and a second condition (shown by dashed lines in FIG. 7), with each condition being analogous to corresponding first and second conditions of the flap version of check structure 118 shown in FIGS. 4–6.

Continuing discussion now with all of FIGS. 4–7, the process of withdrawal and removal of a desired number of devices will be described. The user encounters a desired spooled chain with a terminal, handle-forward device, such as device $108b_1$ (FIG. 4) of middle-positioned, spooled chain 108b in section 104b, extending upwardly through opening 116 in a hand- or hemostat-accessible position behind the front of container 102. The way in which that terminal, handle-forward device is left in such position will be discussed below. In the condition now being described, the size-specific group of ligator tools associated with the particular handle which is exposed is just slightly exposed on the outside of the container, and is in a condition not yet handled by the user of the system.

To withdraw and remove, say, just device $108b_1$, the user (orthodontist or assistant) accesses the handle of that device and pulls it forward of the container over slot $110b_1$. While pulling the device forwardly, the user also pulls it downwardly somewhat after the handle clears the slot. By so pulling, the finger portion feeds through the slot until further movement is resisted when the handle of the next device in the chain is blocked from exiting the slot due to its width being greater than the width of the slot. This very situation is depicted in FIG. 6 with device $108c_1$ having been drawn through slot $110c_1$ until the handle of next device $108c_2$ is resistively blocked from exiting the slot due to the width of the slot being narrower than that of the handle. The spaced handles in the chain thus both visually index the chain length into individual groups, each with a small pre-selected number of units (tools), and physically index dispensing of the respective groups as successive handles are drawn into resistive engagement with the sides of a slot in the anvil.

To cut-separate device $108c_1$ from chain 108c, the user pulls that device downwardly so that its weakened region, such as previously mentioned regions 22 of FIGS. 1–3, is severed by blade 114. The remainder of the chain will stay behind the front of the container, "locked" in place by the check structure, and next device $108c_2$ will now be the terminal device in the chain, with its cut region protruding through slot $110c_1$ like the cut region of device $108a_1$ shown in FIG. 4. With "locking in place", so-to-speak, occurring by pinching, as shown, between the narrow end of a flap or a paddle and the broad confronting face in anvil 117, any tendency of a chain to slip downwardly (by gravity, for example) causes pinch-locking action to intensify and increase. It is for this reason that the check structure of this invention can be thought of as working with toggle-like action.

Still referring to FIG. 6, the user may now leave the remaining amount of the cut region protruding from slot $110c_1$, such as the remaining amount of device $108a_1$ shown in FIG. 4. In addition, the user may choose to grab that remaining amount by using a hemostat and then, to pull that remaining amount up and out of access opening 116 but behind anvil-like structure 117 to reveal a portion of device $108c_2$ similar to the portion of device $108b_1$ shown in FIG. 4.

Of course it should be appreciated that any number of devices may be index-dispensed as described above. Key features of such dispensing are that one-handed dispensing is achieved, and that only the handle of the terminal device in a chain need be handled by the user. The above-described presenting/dispensing system also offers the advantage of preserving usability of unremoved devices in a chain, because such devices are not allowed to move forward of the container into the at-risk, contamination-causing environment.

In the dispensing process just described, and reiterating earlier discussion herein, the handle portions, during pull-up-and-out-dispensing, act as a physical positioning (indexing) structure—such functionality forcing somewhat of a "pause" between exposure of adjacent devices, thus to inhibit undesired exposure of a not yet-to-be-used device. In addition, the handle portions also act as a visual indexing means—serving as a quick visual reference to the user of exactly how many available ligators have been exposed.

It should now be apparent, from the description which has just been given above, that the system of, and the devices provided in, the present invention offer many advantages. The individual devices are formed conveniently with a carrier body that includes a user-manipulable bar-like handle from which projects a slender finger portion containing a pre-selected small number of ligators that can be used conveniently in low-number ligation procedures. Conveniently, these units are formed homogeneously in an elongate chain which can be dispensed from a spooled or folded condition stored within the anti-contamination environment of a protective container.

Device-by-device dispensing is especially facilitated by the positioning coordination and cooperation which occurs between the presentation/dispensing aperture substructure formed in the container in association with each dispensing section, and the respective handle portions formed in the devices. Further, handle structure exposed on the outside of the dispensing container during dispensing action offer a quick visual index and reference to a user of just exactly how many ligators (or other tools) have been exposed for separation and use.

Patient cross-contamination is held to a minimum, as is also unnecessary waste of unused but contamination-exposed tools.

While a specific illustration of the invention has been presented herein showing orthodontic ligators as the tools which are carried for use, and while certain other kinds of tools have been mentioned, it should be apparent to those skilled in the art that the apparatus of the invention is useful for the presentation, dispensing and handling of a variety of medical tools.

Accordingly, while a preferred embodiment of the invention has thus been described herein, one skilled in the art will recognize that certain variations and modifications may be made without departing from the spirit of the invention.

We claim:

1. A presenting/dispensing system for chained, interconnected, cut-separable orthodontic/medical devices comprising a container constructed for housing a chain of such devices, and including presenting/dispensing aperture substructure formed therein to allow for presenting such devices and dispensing a desired number of the same, and toggle-action check structure associated with said aperture substructure, and being changeable, as a result of dispensing action, between a first condition that accommodates dispensing by outward withdrawal of such devices from said container, and a second condition, upon termination of such action, that resists slipping of the remaining chain of devices back into the container, said check structure including an anvil having a broad face, and a swingable flap or paddle having a free end operable to create a pinch/nip region relative to a confronting expanse in said broad face.

2. The system of claim 1, wherein, with said check structure in its said second condition in relation to a chain, any tendency of the chain to slip back into said container causes an increase in the resistive force acting on the chain in said pinch/nip as a consequence of the free end of said flap or paddle drawing closer to said expanse.

3. A presenting/dispensing system for chained, interconnected cut-separable orthodontic/medical devices comprising a chain supply of such devices, a container constructed for housing said chain, and including presenting/dispensing aperture substructure formed therein to allow for presenting the devices in the chain and for dispensing a desired number of such devices, and toggle-action check structure associated with said aperture substructure, and being changeable, as a result of dispensing action, between a first condition that accommodates dispensing by outward withdrawal of such devices from said container, and a second condition, upon termination of such action, that resists slipping of the remaining chain of devices back into the container, said check structure including an anvil having a broad face, and a swingable flap or paddle having a free end operable to create a pinch/nip region relative to a confronting expanse in said broad face.

4. The system of claim 3, wherein, with said check structure in its said second condition in relation to a chain, any tendency of the chain to slip back into said container causes an increase in the resistive force acting on the chain in said pinch/nip as a consequence of the free end of said flap or paddle drawing closer to said expanse.

5. The system of claim 3, wherein each device in a chain contains an indexed number of orthodontic/medical tools.

6. The system of claim 3, wherein each device in the chain includes an associated indexing handle structure.

7. The system of claim 6, wherein said system's aperture structure is designed and sized whereby, during dispensing, successive handle structures in a chain successively resistively encounter the aperture structure.

* * * * *